(12) United States Patent
Souder

(10) Patent No.: US 6,231,497 B1
(45) Date of Patent: May 15, 2001

(54) MAGNETIC THERAPY DEVICE

(76) Inventor: James Souder, 4105 Starboard Ct., Raleigh, NC (US) 27613

(*) Notice: Subject to any disclaimer, the term of this patent is extended or adjusted under 35 U.S.C. 154(b) by 0 days.

(21) Appl. No.: 09/442,156

(22) Filed: Nov. 16, 1999

Related U.S. Application Data

(62) Division of application No. 08/852,543, filed on May 7, 1997, now Pat. No. 6,001,055.
(60) Provisional application No. 60/016,771, filed on May 7, 1996.

(51) Int. Cl.[7] .................................................. A61N 2/00
(52) U.S. Cl. ................................................................ 600/9
(58) Field of Search .......................................... 600/9–15

(56) References Cited

U.S. PATENT DOCUMENTS 4,727,857 * 3/1988 Hori .
5,441,495 * 8/1995 Liboff et al. ............................. 600/9
6,001,055 * 12/1999 Souder ..................................... 600/9

* cited by examiner

Primary Examiner—John P. Lacyk
(74) Attorney, Agent, or Firm—Gifford, Krass, Groh, Sprinkle, Anderson & Citkowski, P.C.

(57) ABSTRACT

The present invention is a magnetic therapeutic device which subjects a treatment area such as an anatomical area or plant to a dynamic magnetic field having an amplitude of at least a half waveform. To subject the treatment area to such a dynamic magnetic field, the magnetic source may be rotated, oscillated, moved through a particular pattern, or otherwise moved relative to the treatment area. Each embodiment of the present invention includes at least one permanent magnet contained within a housing having an application surface which is adapted to engage a treatment area such as an anatomical area of a user's body. The application surface is positioned relative to the magnet so that the magnetic field extends around and/or through the application surface to the anatomical area to be treated. Each magnet has a north and south magnetic pole and a pole width equal to the width of the magnet at the poles. Means for moving the permanent magnet are provided in each embodiment, and are preferably positioned within the housing.

15 Claims, 7 Drawing Sheets

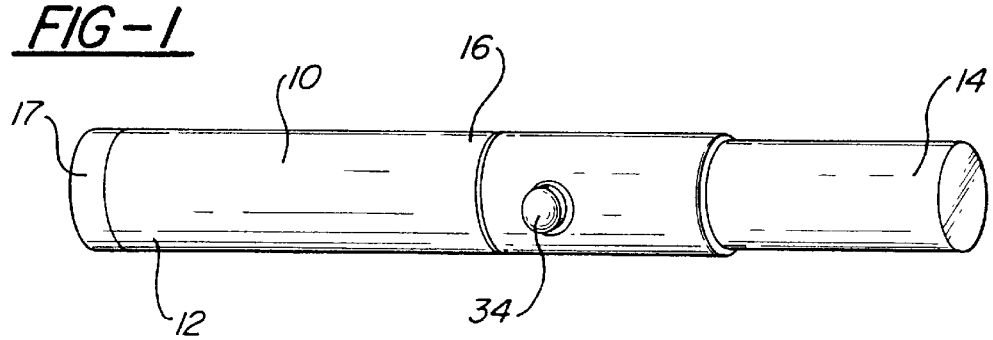
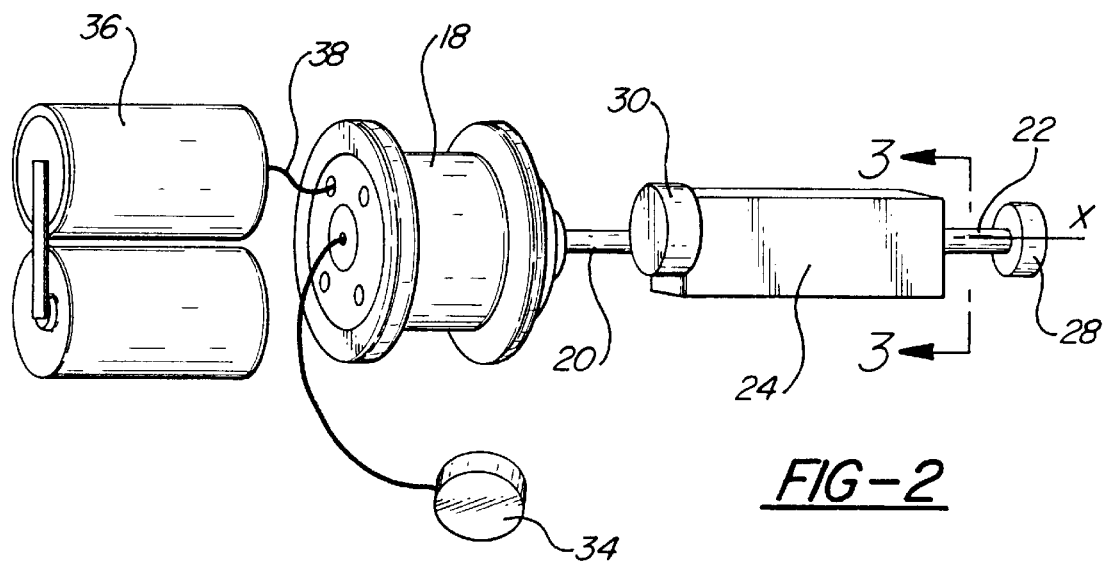
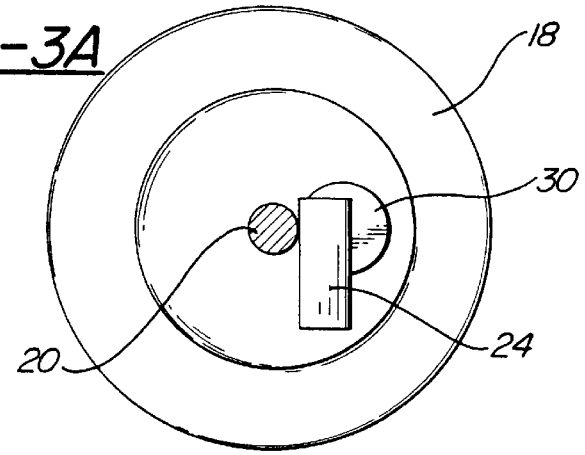

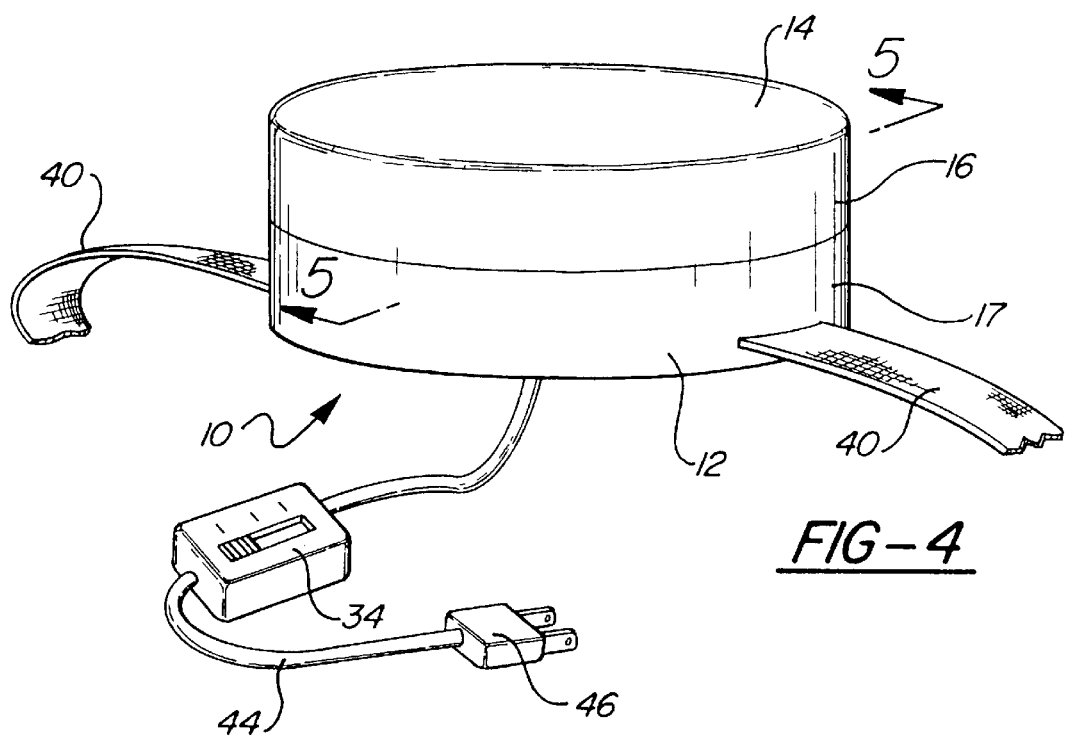
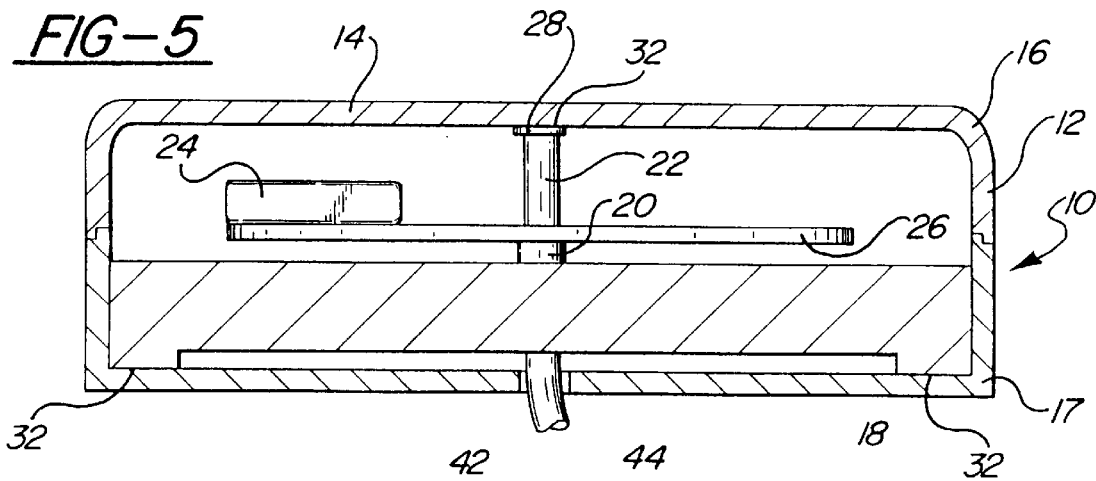

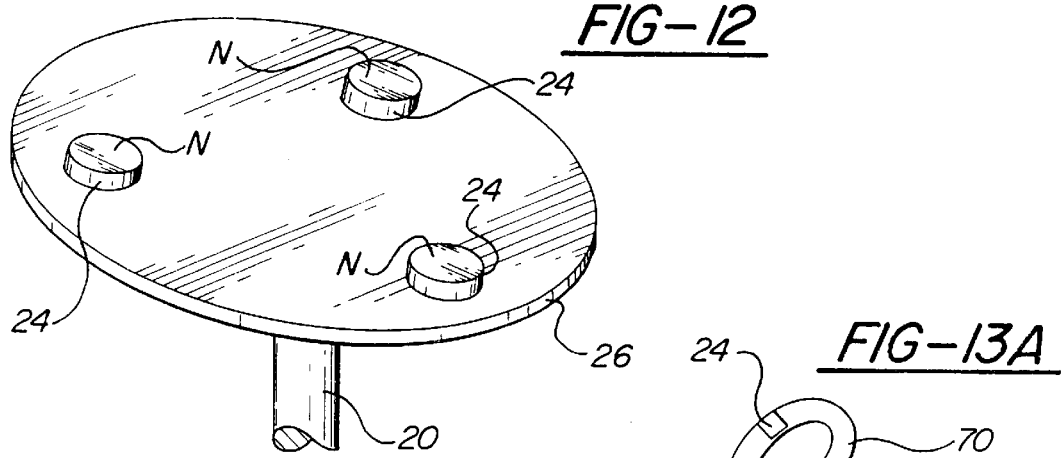
FIG-12
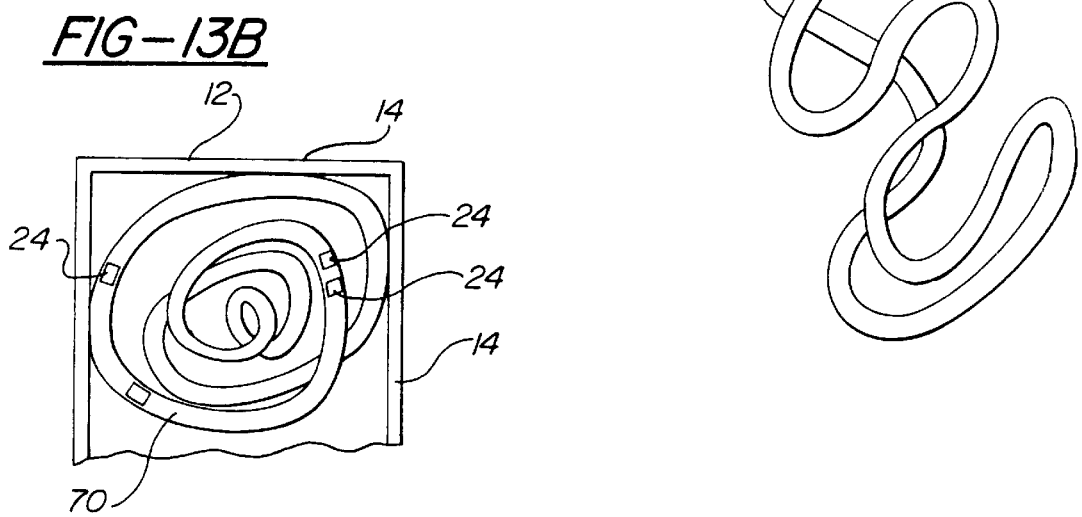
FIG-13A
FIG-13B
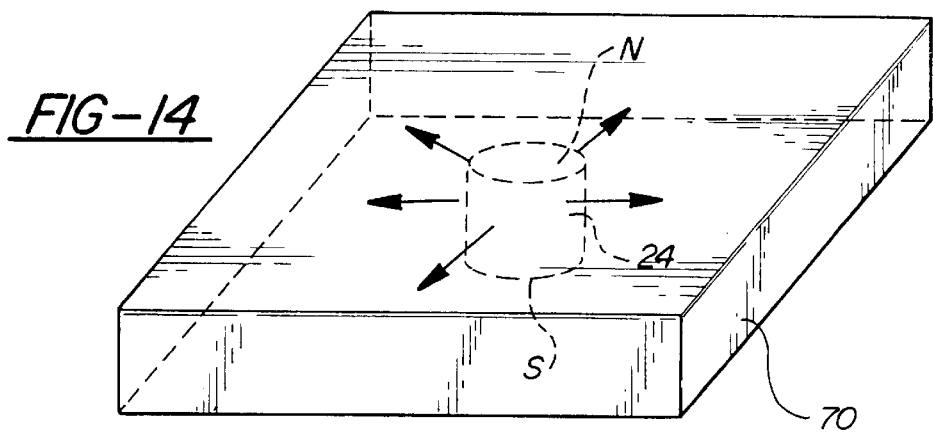
FIG-14

MAGNETIC THERAPY DEVICE

RELATED APPLICATIONS

This application is a divisional application of U.S. application 08/852,543 filed May 7, 1997, now U.S. Pat. No. 6,001,055 which claims the benefit of U.S. Provisional Application 60/016,771 filed May 7, 1996, of which both are incorporated herein by reference.

FIELD OF THE INVENTION

The present invention relates generally to therapeutic devices, and more particularly to such therapeutic devices which utilize dynamic magnetic fields.

BACKGROUND OF THE INVENTION

The beneficial effects of applying a magnetic field to an area of human and animal anatomy such as the back, legs, arms and the like, are widely known and well documented. Magnetic fields are commonly used for therapeutic purposes such as reduction of inflammation in tissues and pain relief. Magnetic fields are known to improve the blood flow to tissues to which the magnetic field is applied. Additionally, the application of magnetic fields to plants is likewise believed to have a beneficial effect on plant growth.

To enhance such beneficial effects, a dynamic magnetic field may be applied to the anatomical area to be treated. The relative movement of magnetic fields through treatment area acts on charged particles such as ions and electrons in the treatment area, displacing the positively and negatively charged particles in opposite directions. The movement of ions and charges influences the distribution of ions on cell membranes, thereby affecting the electrical potential on such cell membranes. The movement of electrons results in locally generated eddy currents which affect the cellular functions of muscles, nerves and other tissues. Such eddy currents have been associated with the activation of capillary blood flow, the relaxation of muscle and connective tissue, and the blocking of propagation of pain impulses as well as other nerve functions.

To maximize the displacement of charged particles (maximize electromotive force product), three variables may be manipulated; the intensity of the magnetic field at the treatment site, the rate of change of the magnetic field at the treatment site, and the amplitude of the net change in magnetic flux (or waveform) to which the treatment site is subjected. The intensity of the magnetic field may be varied by varying the strength of the permanent magnet utilized. The rate of change of the magnetic field may be varied by varying the speed at which the permanent magnet is moved relative to the treatment area.

The last listed variable, the amplitude of the net change in magnetic flux, is believed by some practitioners to be the most important variable in the application of magnetic therapy. Permanent magnets have a north pole and south pole, with north pole magnetic flux emanating from the north pole, and south pole magnetic flux emanating from the south pole. An object moving through the magnetic field generated by a permanent magnet from the north pole of the magnet to the south pole of the magnet is subjected first to a full north pole field. As the object moves toward the south pole, the strength of the north pole field decreases until a neutral field is encountered, approximately at the midpoint of the magnet. As the object continues to move toward the south pole, the object is subjected to a south pole field of increasing intensity until the object reaches the south pole of the magnet where it is subjected to a full south pole field. By moving in this fashion, the object is subjected to a "full waveform." Likewise, an object moved from the south pole to the north pole is also subjected to a full waveform. A maximum displacement of the electrical and ionic equilibrium is achieved when the treatment area is subjected to a full waveform, the treatment area experiencing a complete reversal of magnetic flux. An object may be subjected to a "half waveform" by moving the object from a full north pole field to neutral or full south pole field to neutral. Many practitioners believe that subjecting a treatment area to magnetic flux fields consisting of primarily north pole flux (e.g., half waveforms of north pole flux) enhances the therapeutic effect of the treatment on the anatomical area. The amplitude of the change in magnetic flux may be manipulated to provide preferred configurations of magnetic fields to treatment areas.

A wide variety of devices have been used to expose an anatomical area to a moving magnetic field. Unfortunately, none of the prior art devices permit the magnetic field to be particularly configured to meet particular therapeutic needs, such as the application of a magnetic field having substantially all north pole flux to a treatment area.

Another commonly used therapy for treatment of pain and enhancement of muscular relaxation is vibrational massage. The therapeutic effect of vibrational massage on body tissue is well documented. Many therapeutic devices are available which apply vibration to an anatomical area such as the muscles of the lower back to enhance circulation and relax such muscle.

While various prior art devices apply dynamic magnetic fields to various anatomical areas, none of the prior art devices apply a dynamic magnetic field in conjunction with vibratory massage. While each procedure has been utilized to increase blood flow to an effected area, the combination of procedures increases the beneficial effects to the user as the treated area receives both mechanical massage and magnetic stimulation to enhance blood flow.

SUMMARY OF THE INVENTION

The present invention overcomes disadvantages of the prior art by providing a magnetic therapeutic device which subjects a treatment area such as an animal or human target area or plant structure to a dynamic magnetic field having an amplitude of at least a half waveform. In selected embodiments, the dynamic magnetic field is utilized in conjunction with vibratory massage.

To subject the treatment area to a dynamic magnetic field as described above, the magnetic source may be rotated, oscillated, moved through a particular pattern, or otherwise moved relative to the treatment area. Thus, embodiments of the present invention include rotational embodiments wherein the magnetic source is rotated about an axis, oscillatory embodiments wherein the magnetic source is oscillated with respect to the anatomical or other area to be treated, embodiments characterized by free movement of the magnetic source within a container, and patterned movement of the magnetic source contained within a container.

Regardless of the pattern of movement of the magnetic source, each embodiment of the present invention includes at least one permanent magnet preferably contained within a housing having an application surface which is adapted to engage a treatment area such as an anatomical area of a user's body. The application surface is positioned relative to the magnet so that the magnetic field extends around and/or through the application surface to the anatomical area to be treated. Each magnet has a north and south magnetic pole and a pole width equal to the width of the magnet at the poles. Means for moving the permanent magnet are provided in each embodiment, and are preferably positioned within the housing.

The various rotational embodiments of the invention comprise a permanent magnet mounted on a shaft which is rotated by a motor. The motor, shaft and magnet are enclosed in the housing, the motor being mounted to the housing. In the preferred rotational embodiment, a ferromagnetic metal block is attached to either the north or south pole face of the magnet. The ferromagnetic block acts as a magnetic shunt channeling the flux directly into the covered pole, thereby altering the distribution of flux traveling through air or space directly above either pole. All magnets are bi-polar devices with a north and south pole face 180° out of phase. Normally a symmetrical flux pattern extends into space equidistant from both poles. A paramagnetic shunt provides a less resistive pathway for flux lines than air, and as a result can be used to shape the geometry of a magnetic field in space. Flux emanating from a north pole will project out into space beyond the north pole by nominally five inches in a typical embodiment from whence the flux must complete a magnetic circuit and return via the south pole, actually returning to its point of origin within the magnet. A sufficiently massive paramagnetic pole piece covering the south pole will conduct the returning flux directly into the south pole, and will prevent this flux from reaching out into space beyond the south pole. Without the pole piece the flux pattern would have been symmetrical and flux in the above example would project five inches out from the south pole face also. For example, if the block is attached to the south pole face of the magnet, the magnet will emanate only north pole flux. Thus, as the ferromagnetic block and magnet spin about the shaft, the treatment area is subjected to a rotating magnetic field having a half wave form of north pole magnetic flux.

In an alternate rotational embodiment, the magnet is eccentrically rotated about the shaft. The eccentric rotation of the permanent magnet transmits vibration to the housing and application surface and imparts vibration to the anatomical area being treated. Preferably, an eccentrically mounted weight is positioned on the shaft so that, as the motor spins the shaft, the eccentric movement of the weight and magnet transmits sufficient force to the housing through the connection to the motor, causing the housing to vibrate. The magnetic element may be eccentrically mounted to the shaft, thereby eliminating or reducing the need for an additional eccentric weight.

The rotation of the magnet about the shaft subjects the treatment area to a full waveform and maximum variation of the amplitude of the magnetic field. The application of a full wave form in combination with vibratory massage may be preferred in some treatment regimens.

Additionally, the vibratory massage also provides tactile feedback regarding where the treatment device is being applied.

In yet another rotational embodiment, a ferromagnetic block may be added to the second rotational embodiment having an eccentrically rotated permanent magnet. Thus, a treatment area may be subjected to a rotating magnetic field having a half wave form simultaneously with vibratory massage. Preferably, the ferromagnetic block is configured to enhance or replace the eccentric weight.

In the oscillatory embodiments of the present invention, a fixed arrangement of permanent magnets is positioned within the housing, the arrangement being oscillated with respect to the anatomical area to be treated. Means for oscillating the arrangement of magnets is provided and is preferably positioned within the housing.

In a first oscillatory embodiment, a plurality of magnets are fixedly mounted on a supporting plate, the magnets being spaced apart from each other so that the each magnet is spaced apart from the next nearest magnets by at least one pole width. Each magnet may be positioned so that the upwardly facing pole of each magnet is the same. For example, in one configuration, the north pole face of each magnet is mounted to the supporting plate. In an alternate configuration, the south pole face of each magnet is mounted to the supporting plate. By laterally displacing magnets so arranged proximate to the treatment area, such area is subjected to a repeating half waveform (full north to zero to full north). Preferably, the oscillation additionally imparts vibrational massage to the treatment area. Additionally, the magnets may be mounted on a ferromagnetic plate.

In the second oscillatory embodiment, a plurality of elongated magnetic sources are placed adjacent to each other so that a repeating pattern of alternating magnetic poles are formed, the poles being spaced apart by a predetermined distance. The oscillation of the magnetic sources by a distance equal to or greater than the predetermined distance subjects the treatment area to a complete reversal of magnetic flux, i.e., a full waveform.

Alternate embodiments of the present invention include a container within which at least one permanent magnet is disposed. The container is configured to retain the poles of the magnet in a particular orientation with respect to the treatment area. The container enables the magnet to move freely within a first plane such as a horizontal plane, but prevents the magnet from moving in a second plane such as a vertical plane, the container preventing the magnet from "flipping over." By preventing the permanent magnet from "flipping over," the treatment area is subjected to a magnetic field having a half waveform. The container is positioned proximate to the application surface of the housing and, in selected embodiments, a surface of the container may constitute an application surface.

Embodiments of the present invention which include patterned movement of the magnetic source relative to the treatment area include embodiments where a permanent magnet is moved through a contoured container such as an elongated cylindrical closed tube. In the preferred embodiments, the tube is formed into a path having a non-linear, geometric, linear or other shape. The permanent magnets may be moved through such contoured containers by a variety of means, including pneumatic pressure and the like. Alternate embodiments which include patterned movement of a permanent magnet include means, such as a series of cams and gears, for moving the magnet through a repeating pattern. For example, the magnet may be attached to a cam, providing asymmetrical movement of the magnet with respect to the treatment area. Each embodiment which includes patterned movement of the magnetic source relative to the treatment area may provide for the application of a full waveform or half waveform to such area.

The various embodiments of the present invention may also include means such as straps or a flexible casing for removably affixing the application surface to an anatomical area such as an arm, leg or back.

Other objects, advantages and applications of the present invention will be made clear by the following detailed description of a preferred embodiment of the invention. The description makes reference to drawings in which:

BRIEF DESCRIPTION OF THE DRAWING

FIG. 1 is a perspective view of the preferred embodiment of the invention;

FIG. 2 is a perspective view of selected elements of the embodiment depicted in FIG. 1;

FIG. 3A is a partial cross-sectional end view of the components depicted in FIG. 2 taken along lines 3—3;

FIG. 4 is a perspective view of an alternate embodiment of the invention;

FIG. 5 is a cross-sectional view of the embodiment depicted in FIG. 4 taken along lines 5—5;

FIG. 12 is a perspective partial view of a plurality of magnets mounted to a rotating disk;

FIG. 13A is a perspective view of a container of the present invention;

FIG. 13B is a partial cross-sectional view of an alternate embodiment of the present invention; and FIG. 14 is a perspective view of another container which may be utilized in the present invention.

DETAILED DESCRIPTION OF THE PREFERRED EMBODIMENTS

The invention described herein is a therapeutic device, shown in the attached figures at 10, for applying a dynamic magnetic field to an area to be treated, such as an anatomical area of a human or animal, or a plant, seed, seedling or the like. Each therapeutic device 10 includes at least one permanent magnet 24 having north and south magnetic poles, designated as "N" and "S", respectively. Each magnetic pole has a pole width, designated as "D," the pole width being equal to the width D of the magnet 24 at that pole. While irregularly shaped magnets may be utilized in the various embodiments of the present invention, magnets having a uniform pole width are preferred in this embodiment of alternating poles.

Each therapeutic device 10 includes elements which act in concert to laterally displace the magnet relative to the treatment area by a distance equal to at least the pole width D of the permanent magnet. These elements are described in detail below. In certain embodiments (i.e., FIG. 10), the treatment area is exposed to a half waveform of magnetic flux. In other embodiments (i.e., FIG. 11), the treatment area is exposed to a fall waveform of magnetic flux. Still other embodiments may permit treatment area to be exposed to either a half or full waveform.

Figure 11:
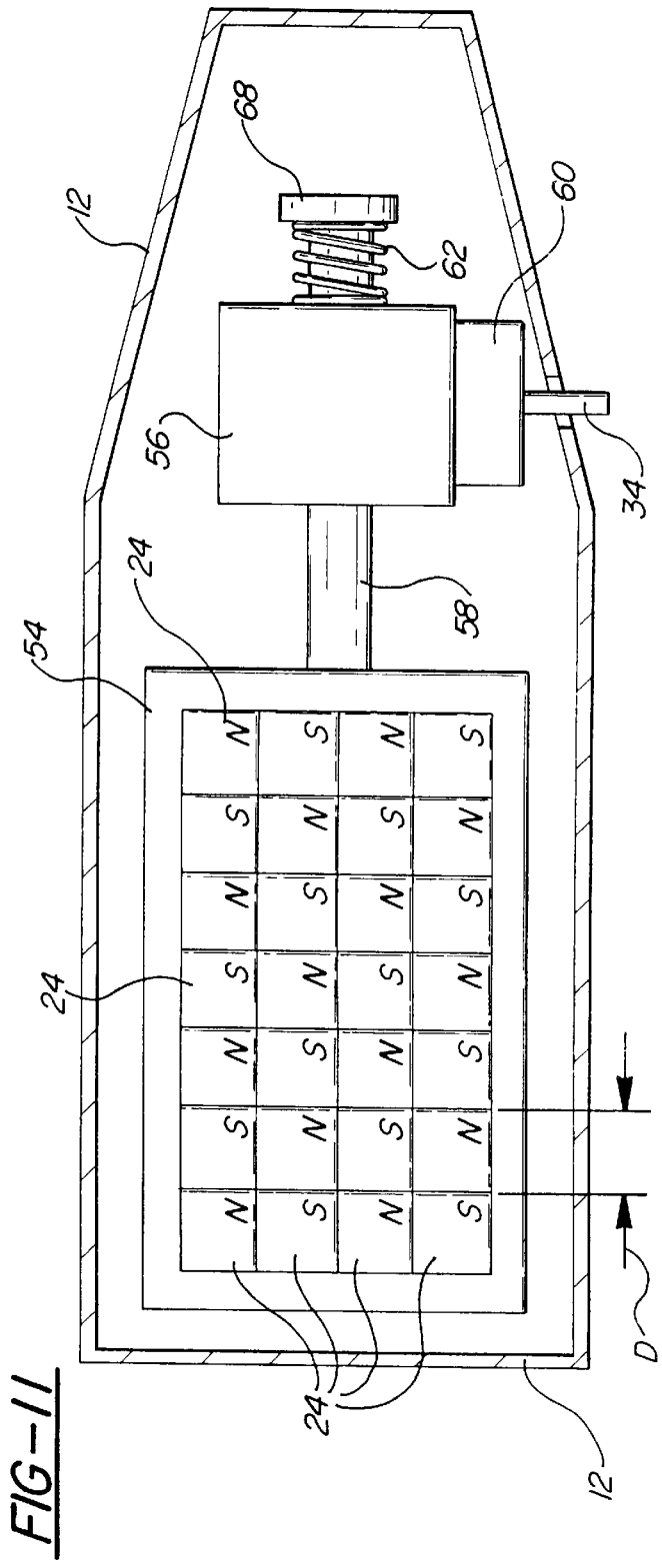
FIG. 11 is a partial cross-sectional top view of another alternate embodiment of the invention.

For example, the device of FIG. 11 may be used to subject the treatment area to a complete reversal of magnetic flux, i.e., a full waveform, by subjecting the treatment area first to a full north pole field. Magnet 24 may be moved relative to the treatment area by a distance equal to one-half of the distance D so that the strength of the north pole field decreases until a neutral field is encountered, approximately at the midpoint of the magnet. As the magnet 24 continues to move laterally through the distance D, the treatment area is subjected to a south pole field of increasing intensity until the treatment area is subjected to a full south pole field.

Figure 6:
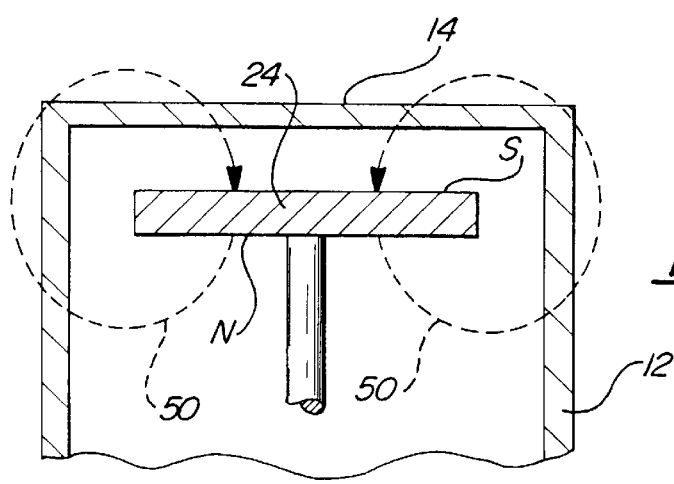
FIG. 6 is a view of the magnetic flux lines in an embodiment of the present invention.
Figure 7:
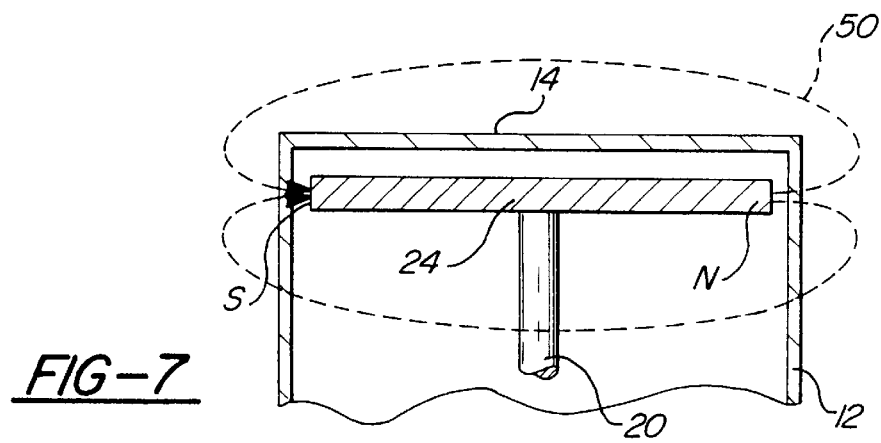
FIG. 7 is a view of the magnetic flux lines of an alternate embodiment of the invention.
Figure 8A:
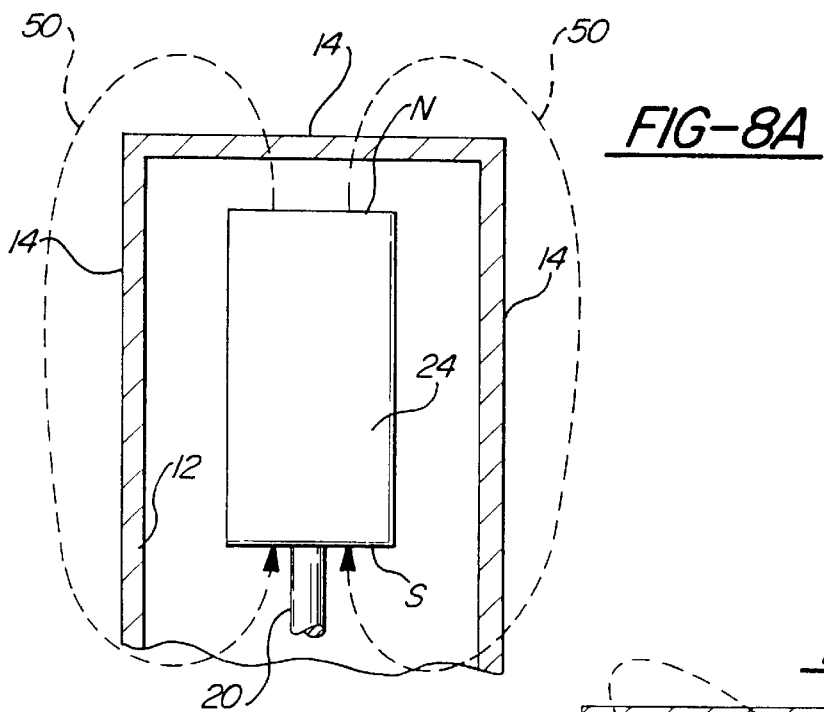
FIG. 8A is a view of the magnetic flux lines in another embodiment of the present invention.
Figure 8B:
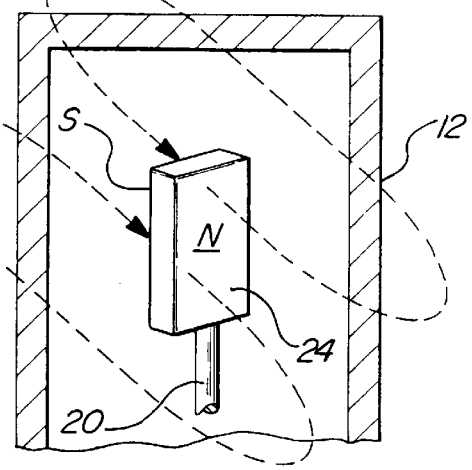
FIG. 8B is a view of the magnetic flux lines in yet another embodiment of the present invention.

Each therapeutic device 10 includes a surface 14 adapted to engage a treatment area to impart dynamic magnetic flux to such area. The surface 14 is located relative to the permanent magnet 24 so that the magnetic flux of the magnet extends beyond the surface 14. The relative position of magnet 24 and surface 14 are depicted in FIGS. 5, 6, 7, 8, 10 and 13B. FIGS. 6, 7 and 8 depict the lines of magnetic flux 50 as they penetrate and/or extend around surface 14. In FIG. 6, magnet 24 is positioned above and substantially parallel to surface 14, the upper surface of magnet 24 being the south pole, the lower surface of magnet 24 being the north pole. Magnetic flux lines 50, emanating from the north pole of magnet 24, penetrate surface 14. FIG. 7 depicts a magnet 24 which is also positioned above and substantially parallel to surface 14, the magnet in FIG. 4 having its north pole positioned at the rightmost edge of magnet 24, the leftmost edge of the magnet 24 being the south pole of the magnet. Magnetic flux lines 50 emanate from the north pole, encircling rather than penetrating surface 14. FIG. 8 depicts an embodiment of the present invention whereby the magnetic flux lines 50 penetrate and encircle different portions of surface 14. It is to be understood that a wide variety of magnetic flux patterns may be utilized in conjunction with the present invention without departing from the scope or spirit of the invention.

Embodiments of the present invention depicted in FIGS. 1, 2, 3A–E, 4, 5, 6, 7, 8A–B and 12 include elements which act to rotate the magnet 24.

The device 10 shown in FIG. 1 includes a permanent magnet 24 mounted to a shaft 20 which extends outwardly from a motor 18. In the preferred embodiment, the magnet 24 is eccentrically mounted to shaft 20. Motor 18 imparts a rotary motion to shaft 20 so that shaft 20 spins about its longitudinal axis X. Motor 18, shaft 20 and magnet 24 are enclosed in a housing 12, the motor 18 being rigidly mounted in the interior cavity 13 of housing 12 by a mechanical connection 32. A variety of semi-rigid mechanical connections 32 may be used to mount motor 18 within housing 12, such as bolting, riveting, or forming the interior surface of housing 12 to fixedly engage the exterior configuration of motor 18.

Housing 12 has an upper portion 16, a lower portion 17, and a surface 14 which is adapted to engage an anatomical area of the user's body to which the therapeutic benefits of vibration and dynamic magnetic fields is required. Upper portion 16 and lower portion 17 are releasably secured to each other so that the elements positioned within the interior cavity 13 of housing 12 are accessible, simplifying assembly and repair of such components. Any conventional means may be utilized to releasably secure upper portion 16 to lower portion 17, such as screws, plastic locking members integrally formed in the housing portions or the like.

As shown in FIG. 3A, a weight 30 is also eccentrically mounted on shaft 20. The size of weight 30 may be varied to increase or decrease the amplitude of vibration of surface 14. As shaft 20 rotates, the magnet 24 and weight 30 create vibration which is transmitted via the rigid mechanical connection 32 to housing 12. A user simply positions the surface 14 adjacent to the anatomical area to be treated.

The end 22 of shaft 20 may be rotatably mounted to the interior surface 13 of housing 12 to enhance the mechanical rigidity of the connection between the motor 18 and the housing 12. A bearing element 28 may be positioned between the end of shaft 22 and housing 12 to reduce wear on motor 18.

In the embodiment depicted in FIG. 1, the surface 14 is cylindrical in shape and may be placed against a user's arm, calf, back muscle or the like. The surface 14 is positioned relative to magnet 24 so that the magnetic flux lines extend beyond surface 14 into the anatomical area to be treated. The strength of the magnet 24 may be varied to accommodate varying configurations of housings 12 and surfaces 14.

Figure 3B:
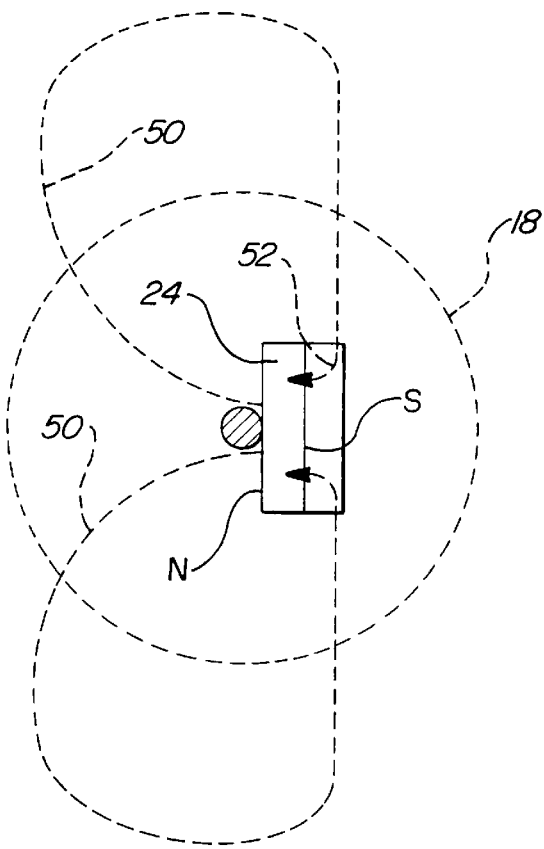
FIG. 3B is a partial cross-sectional end view of an alternate embodiment of the invention.

In the preferred rotational embodiments, a ferromagnetic metal block 52, composed of iron, steel or the like, is attached to either the north or south pole face of the magnet 24. Block 52 preferably has a rectangular cross sectional area and is at least as large as magnet 50, although square and other cross-sectional areas may be utilized. Alternate configurations of the block 52 and magnet 24 are depicted in FIGS. 3B–E. The ferromagnetic block 52 acts as a magnetic shunt by channeling the flux lines 50 emanating from the pole to which the ferromagnetic block is attached. An alternate embodiment of the device depicted in FIG. 2 is depicted in FIG. 3B. A block 52 has been positioned adjacent to the north pole face of magnet 24. The north pole flux, indicated by lines 50, extend beyond motor 18 through housing 12. Flux lines 50 return through block 52 to the south pole. Flux radiating from the south pole travels through block 52 and does not radiate outside the housing. As a result, the magnet will emanate only north pole flux. Thus, as the ferromagnetic block and magnet spin about the shaft 20, the treatment area is subjected to a rotating magnetic field having a half wave form of north pole magnetic flux.

Figure 3C:
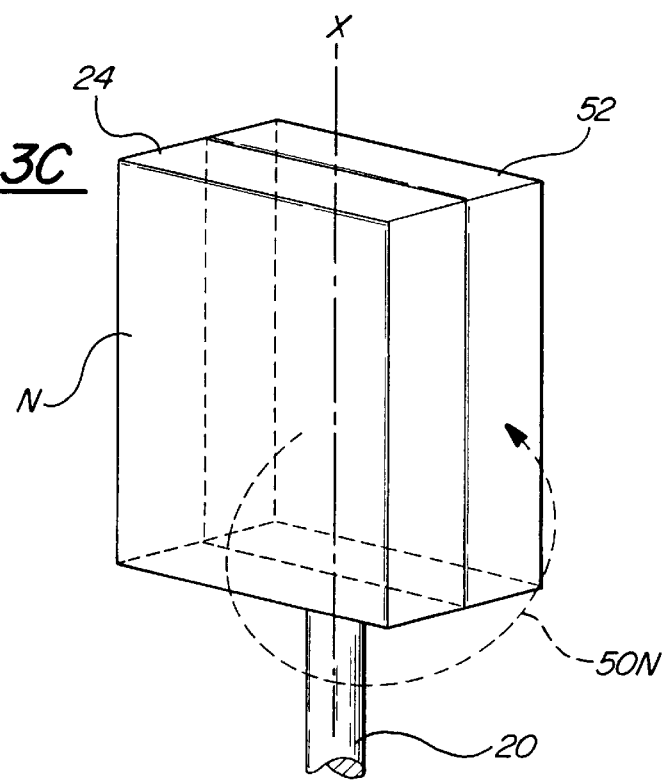
FIG. 3C is an alternate embodiment of the magnet, block and shaft of the present invention.
Figure 3D:
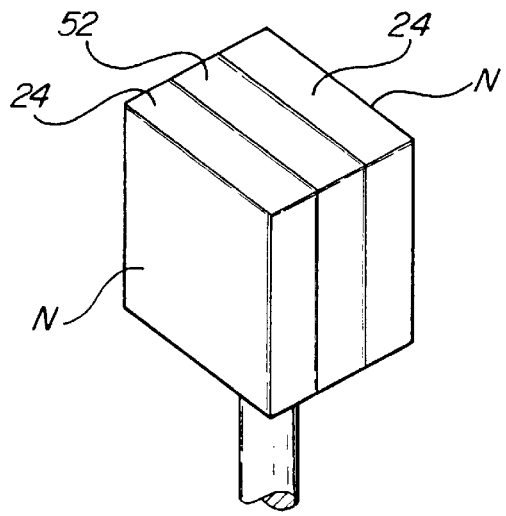
FIG. 3D is another an alternate embodiment of the magnet, block and shaft of the present invention.
Figure 3E:
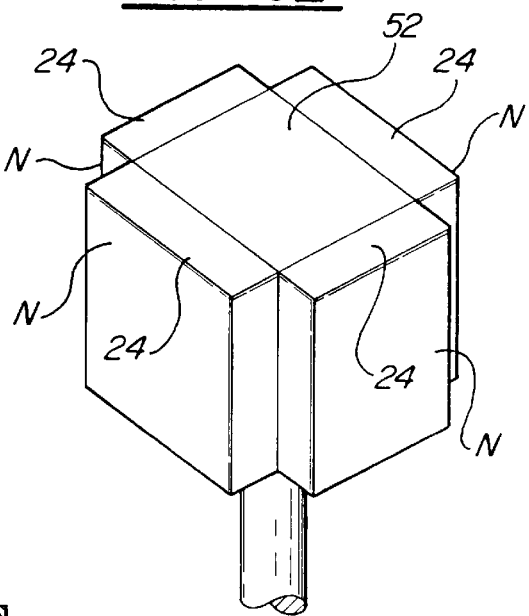
FIG. 3E is yet another alternate embodiment of the magnet, block and shaft of the present invention.

FIGS. 3C–E depict alternate configurations of the magnet 24 and ferromagnetic block 52. FIG. 3C depicts a block 52 mounted to the south pole face of magnet 24, the block and magnet being mounted on shaft 20 and rotatable about axis X. FIG. 3D illustrates an embodiment wherein a ferromagnetic block 52 is positioned between two magnets 24, the magnets 24 being mounted to block 52 along their south pole faces. FIG. 3D depicts yet another embodiment wherein four magnets 24 are mounted to block 52, the south pole faces of each block being mounted to a side of block 52.

Although the housing 12 may be configured in a wide variety of shapes, an alternate embodiment of the present invention depicted in FIGS. 4 and 5 includes a housing 12 having a disk-shaped configuration. The surface 14 of the embodiment depicted in FIG. 4 is substantially flatter than the surface 14 of the embodiment depicted in FIG. 1, enabling the embodiment depicted in FIG. 4 to be used to treat larger anatomical areas of a user, such as the lower or upper back.

Motor 18 may be powered remotely or from a source mounted within housing 12. As shown in the embodiment of FIG. 2, motor 18 may be connected via electrical connections 38 to batteries 36 positioned within housing 12. A switch 34, in electrical communication with motor 18, is preferably mounted in housing 12 and extends exteriorly of the housing so that a user may initiate rotation of magnet 24. There are a variety of suitable methods which are well known in the art for providing power to motor 18. Additionally, pneumatic, spring, hydraulic or other motors may be utilized.

The embodiment depicted in FIG. 4 utilizes a standard electrical receptacle as a remote power source and includes an electrical cord 44 having an electrical plug 46 configured to engage such electrical receptacles. Switch 34 is in electrical communication with cord 44 and may be configured to permit a user to select varying rotational speeds of motor 18 and magnet 24. Thus, the user may vary the vibrational frequency applied to the treatment area by varying the rotational speed of motor 18. Although particular power supplies and switch configurations are depicted with particular embodiments, it is understood that any suitable power supply and switch configuration may be used to operate motor 18 in any embodiment.

Embodiments of the invention may incorporate motors capable of a variety of rotational speeds, thereby permitting adjustment of the dynamic magnetic field. The speed of rotation controls the pulse frequency and amplitude of vibratory massage which stimulates circulation and relaxation of the tissue. Devices of the present invention may utilize a wide variation of rotational speeds while maintaining their therapeutic effect on the treatment area. The preferred embodiment of the present invention utilizes a motor which spins shaft 20 between 400 and 8,000 revolutions per minute. As the rotational speed of permanent magnet 24 was increased from 400 revolutions per minute to 5,000 revolutions per minute, users reported a preferred tactile sensation. Spin rates above 5,000 revolutions per minute and below 400 revolutions per minute may also be utilized where factors dictate optimal frequency.

FIG. 5 is a cross-sectional view of the embodiment of FIG. 4 taken along lines 5—5, depicting the arrangement of the motor 18, shaft 20, and magnet 24 within interior cavity 13 of housing 12. In this embodiment, a disk 26 is mounted on and keyed to shaft 20 so that, as motor 18 rotates shaft 20, disk 26 is rotated at the same revolutions per minute as shaft 20. Magnet 24 is fixedly mounted to disk 26 so that the rotation of disk 26 creates eccentric rotation of shaft 20, causing vibration which is communicated through the rigid mechanical connection 32 of the motor 18 to housing 12 and surface 14. FIG. 12 depicts a plurality of magnets 24 positioned on disk 26 which may be used within the embodiment depicted in FIGS. 4 and 5.

Figure 9:
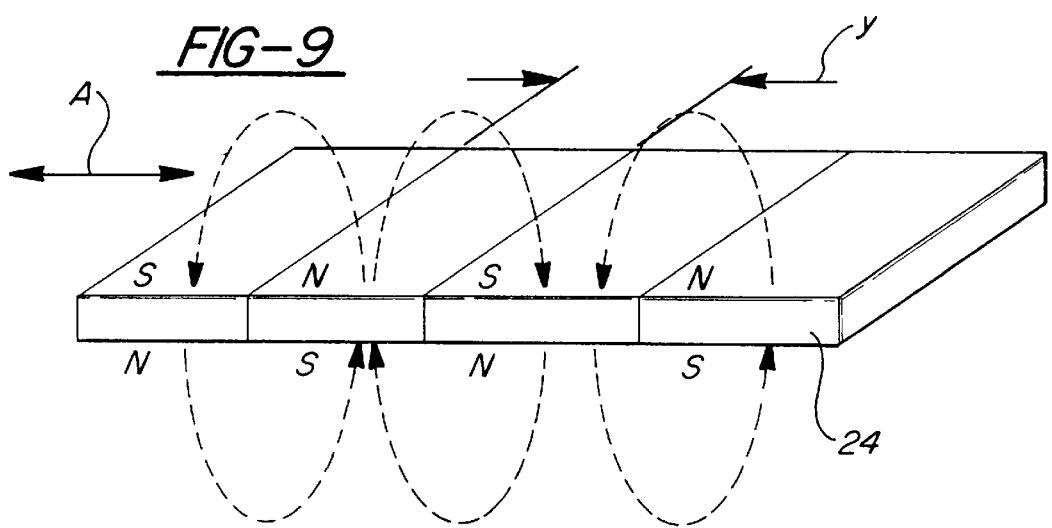
FIG. 9 is a perspective view of an alternate embodiment of the magnet of the present invention.
Figure 10:
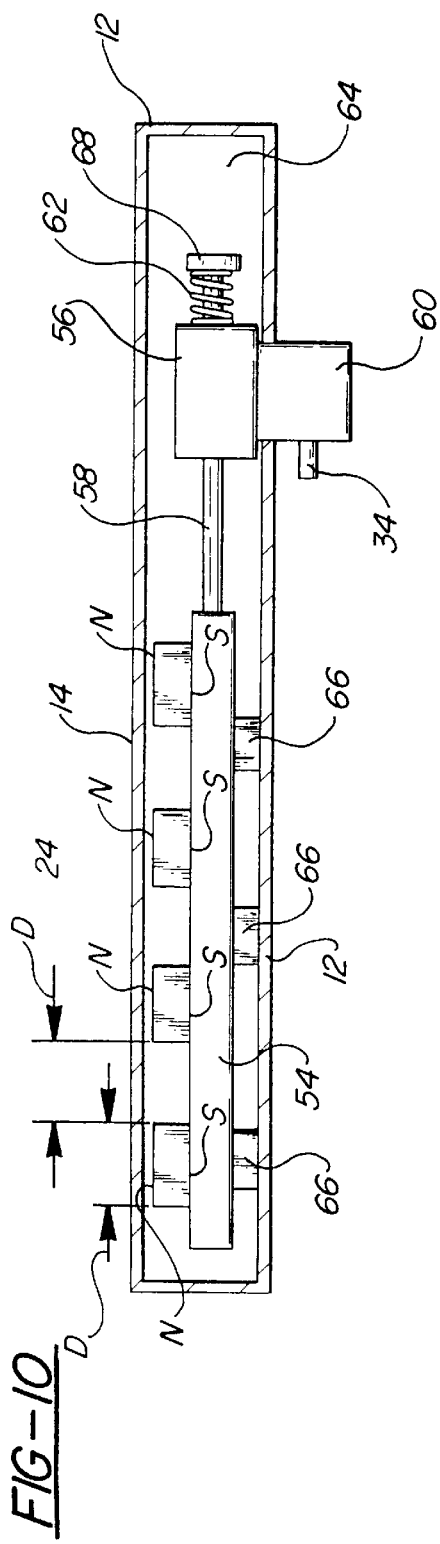
FIG. 10 is a partial cross-sectional side view of an alternate embodiment of the present invention.

FIGS. 9–11 depict embodiments of the present invention whereby the magnet 24 is oscillated with respect to the treatment area. In each embodiment depicted in FIGS. 9–11, a plurality of permanent magnets are mounted on plate 54. If desired, plate 54 may be composed of a ferromagnetic material.

Oscillation of the magnet permits the selection of a particular waveform, whereas rotation of the magnet necessarily requires a full waveform. A full waveform may be selected, the waveform varying between the negative pole and the positive pole. Alternatively, a half waveform may be selected, with the waveform varying between either the negative pole and the neutral or the positive pole and the neutral.

Additionally, the oscillatory movement of the magnets may also be utilized to impart vibration to the treatment area in a manner similar to that described above.

FIG. 10 depicts an oscillatory embodiment of the present invention wherein the magnets are mounted to the plate 54 so that each magnet 24 is spaced apart from the next nearest magnet by at least one pole width D. As shown in FIG. 10, magnets 24 are mounted to the upper surface of plate 54 so that the north pole is facing away from the upper surface of plate 54. Plate 54 is oscillated along the horizontal plane by at least the distance D and preferably by a distance equal to two pole widths by a solenoid motor which includes solenoid 56, power supply 60, switch 34, return spring 62 and stop 68. The elements of the depicted solenoid motor interact in the manner commonly known to those skilled in the art to oscillate the magnets 24 back and forth in a horizontal plane. Other mechanisms may be utilized in the present invention to oscillate magnets 24 in a given plane.

FIG. 11 depicts an embodiment of the invention wherein the permanent magnets 24 are arranged in a checkerboard pattern of alternating north and south poles.

FIG. 9 depicts a magnet 24 comprised of a repeating pattern of alternating magnetic strips having north or south magnetic poles. The magnet depicted in FIG. 9 creates flux lines having centers spaced apart by the distance Y. The oscillation of magnet 24 by a distance equal to or greater than Y subjects the treatment area to a complete reversal of magnetic flux. This motion maximizes the differential of magnetic flux applied to the body portion. The magnet depicted in FIG. 9 may be utilized in any other oscillatory embodiment such as the embodiments depicted in FIGS. 10 and 11.

Alternate embodiments of the present invention include a container, depicted in FIG. 14 at 70, within which at least one permanent magnet 24 is disposed. The container is preferably oscillated by a mechanism such as a solenoid motor, although the container may be moved relative to the treatment area in a variety of ways. The container 70 is configured to retain the poles of the magnet in a particular orientation with respect to the treatment area. The container depicted in FIG. 14 is box-shaped, magnet 24 being disposed therein so that its north pole faces upwardly and its south pole faces downwardly. The container 70 enables magnet 24 to move freely within a first plane such as a horizontal plane, but prevents the magnet from moving in a second plane such as a vertical plane, the container preventing the magnet from "flipping over," subjecting the treatment area which was subjected to north pole flux to be suddenly subjected to south pole flux. By preventing the permanent magnet from "flipping over," the treatment area is subjected to a magnetic field having a half waveform. The container is preferably positioned proximate to the surface 14 of the housing 12 and, in selected embodiments, a surface of the container may constitute a surface 14.

The embodiments depicted in FIGS. 13A and 13B require that the magnet move in a particular pattern through a contoured container. The containers 70 depicted in FIGS. 13A and 13B are elongated cylindrical closed tubes through which at least one magnet 24 moves. In the preferred embodiments, the tube is formed into a path having a non-linear, geometric or other shape. The permanent magnets 24 may be moved repeatedly through such contoured containers 70 by a variety of means, including pneumatic pressure and the like. FIG. 13B depicts container 70 positioned within housing 12, a plurality of magnets 24 contained within and moving through the elongated tube.

Alternate embodiments which include patterned movement of a permanent magnet include means, such as a series of cams and gears, for moving the magnet through a repeating pattern. For example, the magnet may be attached to a cam, providing asymmetrical movement of the magnet with respect to the treatment area. Each embodiment which includes patterned movement of the magnetic source relative to the treatment area may provide for the application of a full waveform or half waveform to such area.

Preferably, neodymium iron boron magnets are utilized in the present invention, for maximum strength, although ceramic magnets, electromagnets or other more powerful magnets may be utilized as they become available. A neodymium magnet having a rectangular shape and spinning on its long axis is preferably utilized in the present invention.

As shown in FIG. 4, straps 40 may be provided to enable a user to place the device 10 proximate to the anatomical area to be treated and affix device 10 in position, enabling the user to perform tasks while receiving the therapeutic benefits of vibratory massage and alternating magnetic fields. The invention may also be constructed as a free standing device or may be incorporated into a pillow, chair or mattress.

Additionally, a plurality of magnets may be used and mounted to shaft 20 to enhance and vary the magnetic flux and vibratory pattern applied to the treatment area.

What is claimed is:

1. A magnetic therapeutic device comprising:
    at least one permanent magnet having north and south poles and a pole width wherein the at least one permanent magnet is mounted to a rotatable shaft having an axis of rotation at an orientation such that therapeutic magnetic flux of said at least one permanent magnet predominantly extends in a plane non-parallel to the axis of rotation;
    at least one ferromagnetic block mounted to said at least one permanent magnet such that the ferromagnetic block is adjacent to a magnetic pole;
    a surface adapted to engage a treatment area to impart magnetic flux to the treatment area, the surface being located relative to the at least one permanent magnet such that the magnetic flux extends beyond the surface; and
    a drive system for rotating said at least one magnet about said shaft.

2. The device of claim 1 wherein said drive system comprises a rotary motor having said shaft extending outwardly therefrom.

3. The device of claim 1 wherein said shaft rotates eccentrically.

4. The device of claim 3 wherein said shaft is a cam shaft.

5. The device of claim 1 further comprising a plurality of magnets mounted on a plate.

6. The device of claim 5 wherein the plate is a ferromagnetic plate.

7. The device of claim 5 wherein said plurality of magnets are arranged in a dimensionally alternating pattern of north and south poles.

8. The device of claim 5 wherein said plurality of magnets are mounted to said plate such that each magnet of said plurality is at least one pole width from another magnet of said plurality.

9. The device of claim 1 wherein said at least one permanent magnet is rectilinear in cross section orthogonal to the axis of rotation.

10. A magnetic therapeutic device comprising:
    a plurality of magnets each having north and south poles and a pole width wherein said plurality of magnets is mounted to a rotatable shaft having an axis of rotation at an orientation such that therapeutic magnetic flux of said plurality of magnets predominantly extends in a plane non-parallel to the axis of rotation;

a surface adapted to engage a treatment area to impart magnetic flux to the treatment area, the surface being located relative to said plurality of magnets such that the magnetic flux extends beyond the surface; and a drive system for rotating said plurality of magnets about said shaft.

11. The device of claim 10 further comprising: at least one ferromagnetic block mounted to said at least one of said plurality of magnets such that the ferromagnetic block is adjacent to a magnetic pole.

12. The device of claim 10 wherein said drive system comprises a rotary motor having said shaft extending outwardly therefrom.

13. The device of claim 10 wherein said shaft rotates eccentrically.

14. The device of claim 10 wherein said plurality of magnets are arranged in a dimensionally alternating pattern of north and south poles.

15. The device of claim 10 wherein said plurality of magnets are mounted to a plate such that each magnet of said plurality is at least one pole width from another magnet of said plurality.

* * * * *